United States Patent [19]

Nicolaou et al.

[11] Patent Number: 5,274,137

[45] Date of Patent: Dec. 28, 1993

[54] INTERMEDIATES FOR PREPARATION OF TAXOLS

[76] Inventors: K. C. Nicolaou, 9625 Blackgold Rd., La Jolla, Calif. 92037; Chan-Kou Hwang, 5035 Camino Playa Malaga, San Diego, Calif. 92124; Erik J. Sorensen, 3959-C Miramar St.; Jin-Jun Liu, 9528 Poole St., both of La Jolla, Calif. 92037

[21] Appl. No.: 902,390

[22] Filed: Jun. 23, 1992

[51] Int. Cl.$^5$ .............................................. C07D 305/14
[52] U.S. Cl. ..................................... 549/510; 549/511
[58] Field of Search ................................ 549/510, 511

[56] References Cited

PUBLICATIONS

A. S. Kende, et al., "Synthesis of a Taxane Triene," J. Am. Chem. Soc., (1986) 108, 3513–3515.

L. Pettersson, et al., "An Enantiospecific Synthesis of a Taxol A-Ring Building Unit," Tetrahedron Letters, vol. 28, No. 24, pp. 2753–2756, (1987).

Y. Ohtsuka, et al., "Synthesis of 3,8,11,11-Tetramethyl-4-oxobicyclo[5.3.1] undecane as a Model for Taxane Synthesis," Chem.Pharm.Bull., (1988,) 36, 4711–4721.

I. Kitagawa, et al., "Synthesis of a Chiral 1,1,3-Trimethylcyclohexane Derivative from d-Camphor . . . " Chem. Letters, (1980,) 1001–1004.

C. S. Swindell, "Taxane Diterpene Synthesis Strategies, A Review," Organic Preparations & Procedures, Int., (1991,) 23, 465–555.

*Primary Examiner*—C. Warren Ivy
*Assistant Examiner*—Ba K. Trinh
*Attorney, Agent, or Firm*—Kazuyuki Yamasaki

[57] ABSTRACT

A taxol intermediate selected from the group consisting of:

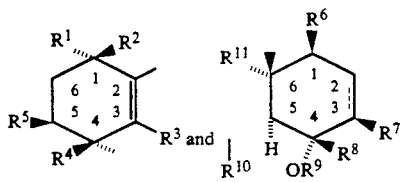

wherein $R^1$ and $R^2$ are the same or different and each selected from hydrogen, hydroxyl, or a protected hydroxyl; or $R^1$ and $R^2$ together form an oxo or a protected oxo; $R^3$ is formyl, a protected formyl, or —CH(X)—OY wherein X is hydrogen or a monovalent metal and Y is hydrogen or a hydroxyl protecting group; and $R^4$ and $R^5$ are different and each selected from chloro or cyano; or $R^4$ and $R^5$ together form an oxo or a protected oxo, with the proviso that $R^1$ and $R^2$ are not both hydroxyl; $R^6$ is hydroxyl or a protected hydroxyl; $R^7$ is hydrogen, hydroxyl, or a protected hydroxyl; $R^8$ is carboxyl, hydroxylmethyl, or a protected hydroxylmethyl; or $R^7$ and $R^8$ when taken together with carbon atoms 3 and 4, form an oxetane ring; or $R^6$ and $R^8$ when taken together with carbon atoms 1 and 4, form a bridged lactone; $R^9$ is hydrogen or a hydroxyl protecting group; $R^{10}$ is hydroxyl or a protected hydroxyl; or $R^8$ and $R^{10}$ when taken together with carbon atoms 4 and 5, form a γ-butyrolactone ring; $R^{11}$ is alkoxycarbonyl, formyl, a protected formyl, hydroxylmethyl or a protected hydroxylmethyl; or $R^6$ and $R^{11}$ when taken together with carbon atoms 1 and 6, form a 2,2-dimethyl-1,3-dioxane ring; and the dotted line between the 2- and 3-positions of the six-membered ring represents an optional bond.

3 Claims, No Drawings

INTERMEDIATES FOR PREPARATION OF TAXOLS

This invention was made with Government support under NIH Grant No. CA46446, awarded by the National Institute of Health. The Government has certain rights in the invention.

BACKGROUND OF THE INVENTION

1. Field of the Invention

This invention relates to novel intermediates for the preparation of taxol and its congeners, a process for their preparation, and a process for the preparation of taxol involving the use of such intermediates or their functionally equivalent molecules.

2. Description of Related Art

Taxol was first isolated in 1971 from the western yew, *Taxus brevifolia* by Wani et al. (*J. Am. Chem. Soc.*, 1971, 93, 2325), who characterized its structure by chemical and X-ray crystallographic methods.

Taxol is a member of the taxane family of diterpenes having the following structure:

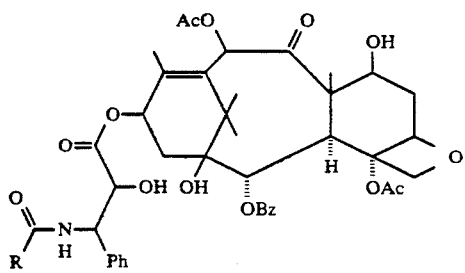

1: Taxol, R = Ph
2: Taxotere, R = O$^t$Bu

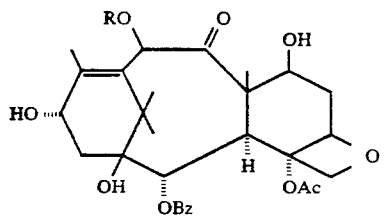

3: 10-Descetylbaccatin III, R = H
4: Baccatine III, R = Ac

Taxol and various taxane derivatives (collectively herein referred to as "taxols") are highly cytotoxic and possess strong in vivo activities in a number of leukemic and tumor systems. Especially, taxol (1) is considered an exceptionally promising cancer chemotherapeutic agent, and is currently in phase II clinical trials in the United States. Equally important is taxotere (2), a semisynthetic analog of taxol which is also undergoing clinical trials with impressive results.

Clinical results have demonstrated high efficacy against such cancer types as ovarian, lung, gastric, breast, colon and cervical carcinomas. However, the major problem with the ongoing clinical trial is the limited availability of the compound. Various techniques for securing a sufficient supply of taxol are the subject of active research. Strategies being studied include total synthesis, partial synthesis (from readily available taxol precursors), extraction from Taxus needles, cultivation of Taxus plants, identification of structurally simpler taxols, and cell culture production.

The only available natural source of taxol to date is several species of very slowgrowing yew (genus Taxus, family Taxaceae). The isolation procedures currently in use are very difficult, low-yielding, and obviously fatal to the source. For example, C.H.O. Huang et al. (*J. Nat. Prod.*, 1986, 49, 665) reported a 0.01% yield from a large scale isolation starting with 806 lbs. or more of *Taxus brevifolia* bark. Other reported yields of taxol from various species of yew range from 50 mg/kg to 165 mg/kg (i.e., 0.005–0.017%).

Because of the structural complexity of taxol, partial synthesis is considered a viable approach to providing adequate supplies of taxol. The first successful partial synthesis of taxol was developed by J. N. Denis et al. in *J. Am. Chem. Soc.*, 1988, 110, 5917; *J. Am. Chem. Soc.*, 1988, 110, 5417; U.S. Pat. No. 4,924,011. The starting materials for the partial synthesis, 10-deacetylbaccatin III (3) or baccatin III (4), can be extracted in relatively high yield from the leaves of Taxus baccata. However, this approach still relies upon the supply of yew leaves, although they are renewable resources, unlike yew bark.

The total synthesis of taxols may provide practical solutions to the problems associated with the isolation method or the partial synthesis. Thus, the total synthesis of taxol has attracted much interest among synthetic organic chemists worldwide. So far, the results have not been entirely satisfactory. One successful example is the work of Holton et al. (*J. Am. Chem. Soc.*, 1988, 110, 6558), wherein a synthesis of the taxol congener-taxusin- is reported. Despite the progress made in this and numerous other synthetic approaches, the final total synthesis of taxol is likely to be a multi-step, tedious and costly process.

The major difficulty involved in the synthesis of taxols resides in the construction of the tricyclic carbon frame, pentadecene, which is shown below:

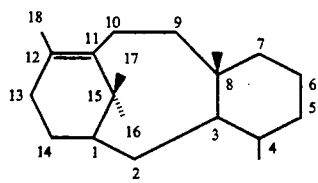

Another difficulty with the synthesis of taxols is the incorporation of abundant oxygen functionalities at positions 1, 2, 4, 5, 7, 9, 10 and 13 of the ring system.

Based on a rational retrosynthetic analysis, the present investigators have identified two key ring units which are provided with oxygen substituents having proper (natural stereochemistry) and which could be easily coupled to form a basic skeleton of taxols. The use of such versatile intermediates allows the synthesis of not only taxol, but also other potential antitumor agents having the pentadecene ring with an array of oxygenated functionalities at various positions.

Consequently, the present invention addresses the much-sought need of availability of key intermediates for the synthesis of taxols, and leads to the ultimate total synthesis of taxol itself.

SUMMARY OF THE INVENTION

This invention is directed to the key intermediates in the synthesis of taxols. Specifically, this invention provides a compound of the formula:

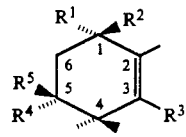

wherein $R^1$ and $R^2$ are the same or different and each selected from hydrogen, hydroxyl, or a protected hydroxyl; or $R^1$ and $R^2$ together form an oxo or a protected oxo; $R^3$ is formyl, a protected formyl, or —CH(X)—OY wherein X is hydrogen or a monovalent metal and Y is hydrogen or a hydroxyl protecting group; and $R^4$ and $R^5$ are different and each selected from chloro or cyano; or $R^4$ and $R^5$ together form an oxo or a protected oxo, with the proviso that $R^1$ and $R^2$ are not both hydroxyl.

This invention also provides a compound of the formula:

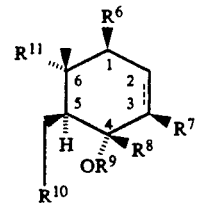

wherein $R^6$ is hydroxyl or a protected hydroxyl; $R^7$ is hydrogen, hydroxyl, or a protected hydroxyl; $R^8$ is carboxyl, hydroxylmethyl, or a protected hydroxylmethyl; or $R^7$ and $R^8$ when taken together with carbon atoms 3 and 4, form an oxetane ring; or $R^6$ and $R^8$ when taken together with carbon atoms 1 and 4, form a bridged lactone; $R^9$ is hydrogen or a hydroxyl protecting group; $R^{10}$ is hydroxyl or a protected hydroxyl; or $R^8$ and $R^{10}$ when taken together with carbon atoms 4 and 5, form a γ-butyrolactone ring; $R^{11}$ is alkoxycarbonyl, formyl, a protected formyl, hydroxylmethyl or a protected hydroxylmethyl; or $R^6$ and $R^{11}$ when taken together with carbon atoms 1 and 6, form a 2,2-dimethyl-1,3-dioxane ring, and the dotted line between the 2- and 3-positions of the six-membered ring represents an optional bond.

This invention further provides a process for the preparation of these key intermediate compounds from readily available starting materials.

Other objects and features of this invention will be apparent from the reading of the Detailed Description of the Invention that follows.

DETAILED DESCRIPTION OF THE INVENTION

This invention is based, in part, on the retrosynthetic analysis of the taxol (1) molecule according to the following scheme:

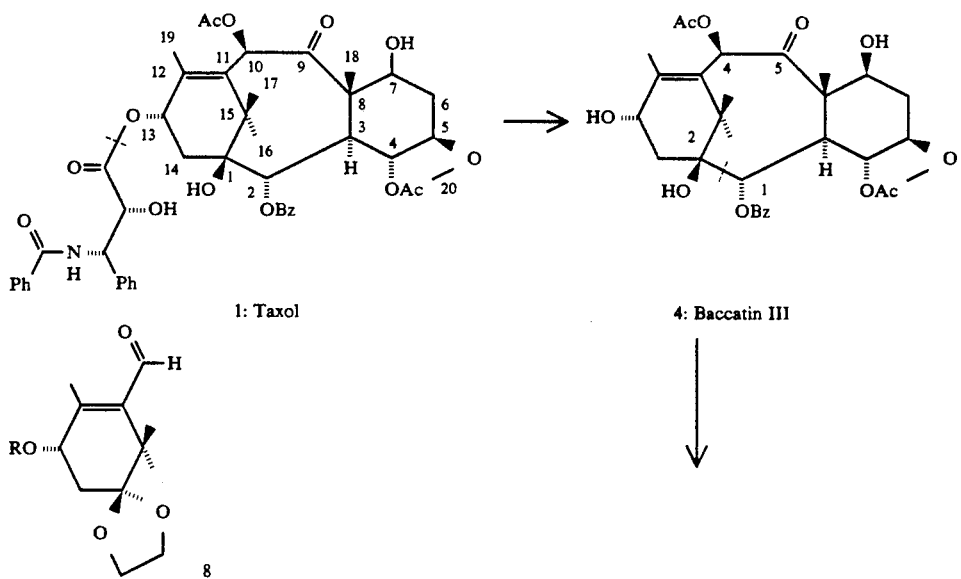

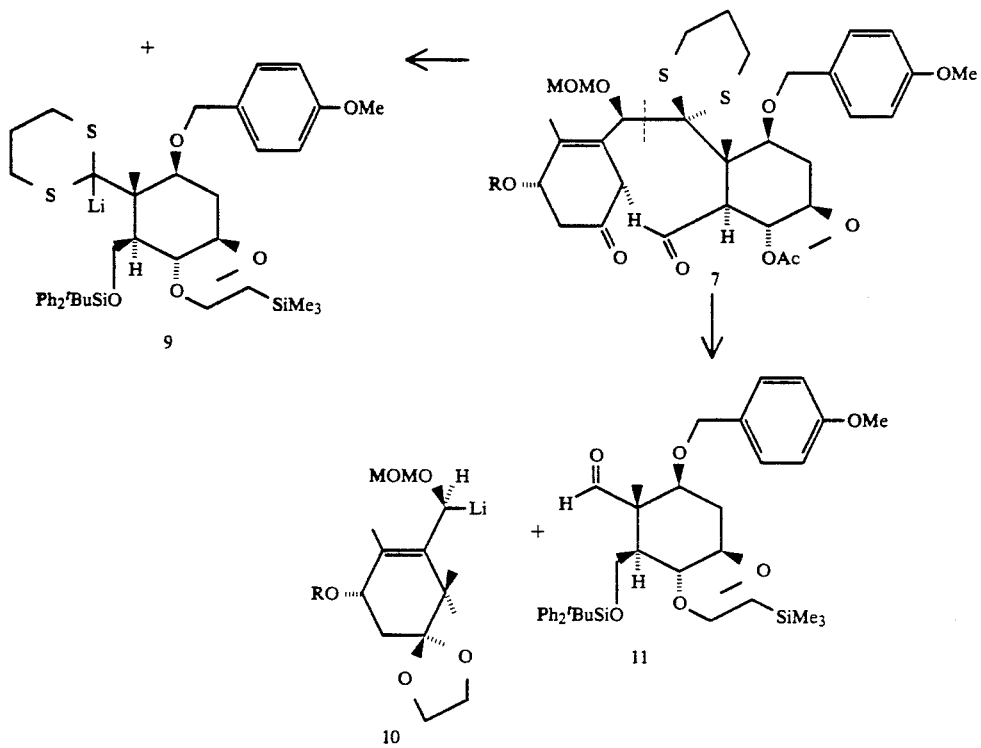

wherein R represents a hydroxyl protecting group; Bz represents benzoyl; and MOM represents methoxymethyl.

Disconnection of the ester side chain [as indicated by a broken line in formula (1)] leads to baccatin III (4). Further disconnection at the C₁—C₂ bond of baccatin III generates a ketoaldehyde (7) as a precursor to the desired ring system. Still further disconnection of the ketoaldehyde (7), as indicated by a broken line, results in a combination of an A ring unit (8) and a CD ring unit (9) or a different combination of an A ring unit (10) and a CD ring unit (11).

First, this invention is directed to compounds of formula (5), the structure of which is depicted hereinbelow.

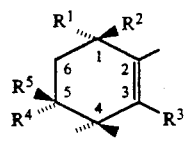

As previously defined, R¹ and R² are the same or different and each selected from hydrogen, hydroxyl, or a protected hydroxyl; or R¹ and R² together form an oxo or a protected oxo; R³ is formyl, a protected formyl, or —CH(X)—OY wherein X is hydrogen or a monovalent metal and Y is hydrogen or a hydroxyl protecting group; and R⁴ and R⁵ are different and each selected from chloro or cyano; or R⁴ and R⁵ together form an oxo or a protected oxo, with the proviso that R¹ and R² are not both hydroxyl.

Thus, the compounds (5) encompass the A ring units (8) and (10) and their functionally equivalent molecules.

Exemplary hydroxyl protecting groups include: alkanoyl having 2 to 5 carbons, such as acetyl; aryloyl having 7 to 11 carbons, such as benzoyl; benzyl; 4-methoxyphenylmethyl; 3,4-dimethoxyphenylmethyl; methoxymethyl; 1-ethoxyethyl; trialkylsilyl, such as trimethylsilyl and tert-butyldimethylsilyl; tert-butyldiphenylsilyl; and the like. Where more than two hydroxyl protecting groups are present in the molecule, it is usually preferred that they be different in order to be chemically distinct.

Exemplary protected formyl groups include 1,3-dioxolanyl, 1,3-dithiolanyl, 1,3-dithianyl and the like. Preferred oxo protecting group is 1,3-dioxolane.

When X is a monovalent metal, lithium is preferred.

A first preferred group of the compounds (5) are those wherein R¹ is a protected hydroxyl, and R² is hydrogen. Especially favored within this group are the compounds wherein R⁴ and R⁵ together form 1,3-dioxolane. Further favored compounds are those wherein R³ is formyl or —CH(Li)—OY wherein Y is a hydroxyl protecting group.

A second preferred group of compounds are those wherein R¹ and R² are both hydrogen. Favored within this group are the compounds wherein R³ is —CH₂—OY wherein Y is a hydroxyl protecting group. Further favored compounds are those wherein R⁴ is chloro and R⁵ is cyano, or R⁴ is cyano and R⁵ is chloro.

Some of preferred individual compounds within the generic formula (5) are depicted hereinbelow:

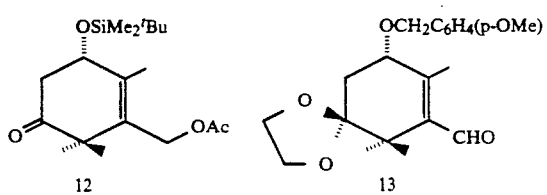

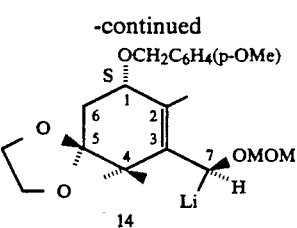

wherein MOM is as previously defined.

Since the compounds of formula (5) may have several asymmetric centers, it is recognized by those skilled in the art that the compounds may exist in diastereomeric, racemic, or optically active forms. All of these forms are contemplated within the scope of this invention. More specifically, this invention includes enantiomers, diasteromers, racemic mixtures, and other mixtures thereof.

In the above formulae (12)–(14), the preferred configuration at the 1-position of the six-membered ring is S. In the formula (14), the preferred configuration at the 7-position (side chain) is also S. The (5S–7S) configurtion corresponds to natural configurations at respective sites in the taxol molecule. The structure of formula (14) depicts this preferred enantiomeric form.

For purposes of illustrative clarity and ease of comprehension, an exemplary synthesis of preferred compounds of formula (12) is illustrated hereinbelow. It should be understood, however, that the description of this particular route shall not restrict nor limit the use of other viable synthetic routes leading to the same or structurally similar compounds. The present scheme can also be used with modifications that are obvious to one skilled in the art to prepare the compounds of formula (5) which differ from those compounds depicted in the scheme.

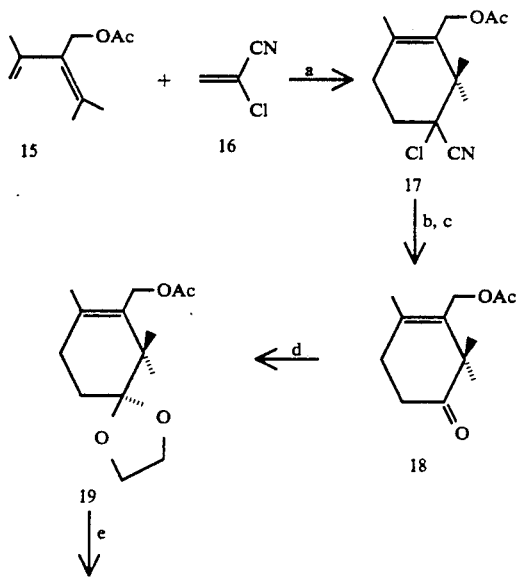

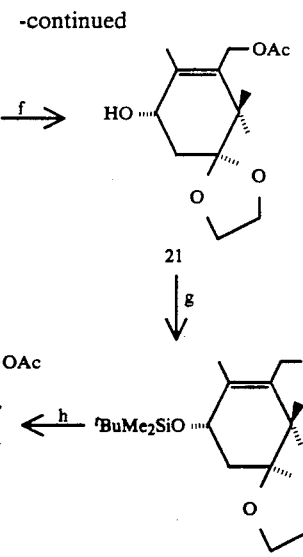

Scheme 1. Synthesis of Taxol Ring A Unit

Reagents And Conditions: (a) 1 eq of (15), 1.5 eq of (16), 135° C., 4 days, 85%; (b) 4 eq of KOH, $^t$BuOH, 70° C., 4 h, 65%; (c) Ac$_2$O, DMAP; (d) 4 eq of ethylene glycol, 0.2 eq of TsOH, benzene, 70° C., 1 h, 92%; (e) 1 eq of SeO$_2$, 1,4-dioxane, 90° C., 2 h, 65%; (f) 0.1 eq of Corey's oxazaborolidine (R), 2 eq of catecholborane, toluene, −78° C., 2 h, 95%, 95% ee; (g) 1.2 eq of $^t$BuPh$_2$SiCl, 1.5 eq of imidazole, DMF, 25° C., 8 h, 90%; (h) 1 eq Ts-OH, acetone, H$_2$O 25° C., 90%.

The starting material of formula (15) can be prepared by conventonal procedures, as reported in I. Alkonyi et al., Chem. Ber., 1967, 100, 2773. The other starting material of formula (16) is commercially available or can be prepared readily.

Among many steps involved in the above sequence, several reactions are considered critical and are worthy of further note.

The first step (a) of the sequence, a Diels-Alder reaction between a diene (15) and a dienophile (16), is conducted generally without a solvent at a teperature from about 100° C. to about 150° C. Under these conditions, reaction is complete within several days. For one mole of the diene (15), it is preferred to use an excess amount (e.g., 50% excess) of the dienophile (16). The reaction is highly regioselective, resulting in the formation of a single regioisomer as depicted in the formula (17), the structure of which has been confirmed by X-ray crystallographic analysis.

Step (f), the conversion of an achiral ketone (20) to a chiral alcohol (21), is conducted in a reaction-inert solvent such as toluene, using Corey's oxazaborolidine reagent (E. J. Corey et al., Tetrahedron Letters, 1990, 5, 611). This asymmetric reduction is conducted at temperatures ranging from about −78° C. to ambient temperature. Reaction times of a few hours (e.g., two hours) are commonly used. The use of a chiral oxazaborolidine (R) in the presence of catecholborane achieves a highly enantioselective preparation of the S alcohol, as depicted in formula (21), normally over 98% ee.

All the products of formulae (17) through (12) including (17) and (21), in the sequence can be isolated and purified by conventional means.

The chiral alcohol of the formula (21) can be readily converted to an aldehyde of formula (13) or an equivalent molecule thereof (Ring A units). Thus, protection of the C$_1$-alcohol as a 4-methoxyphenylmethyl ether and deprotection of the acetyl group from the side-chain primary hydroxyl, followed by manganese dioxide oxidation, affords the aldehyde (13), Additionally, the compund of formula (14) can be prepared from the aldehyde (13), first by conversion of the formyl group into a stannyl ketone such as tri-butylstannyloxo, and second by asymmetric reduction of the oxo group followed by protection of the resultant hydroxyl. The stannylation reaction can be carried out by the method described in J. A. Marshall et al., *Tetrahedron Letters*, 1989, 20, 2183, using tri-n-butylstannyllithium in tetrahedrofuran at −78° C. and azodicarbonyl dipiperidide. The asymmetric reduction can be carried out by the method described in R. Noyori et al., *J. Am. Chem. Soc.*, 1984, 106, 6709; and ibid, 1984, 106, 6717; using (R)-(+)-Binal-H. Protection of the C$_7$-hydroxyl with a suitable group such as methoxymethyl and transmetalation with n-butyllithium, which replaces the stannyl group by lithium, provides the desired ring A unit (14) with the desired natural configuration S at the 10-position of the taxol skeleton.

Secondly, this invention is directed to the compounds of formula (6), the structure of which is depicted hereinbelow.

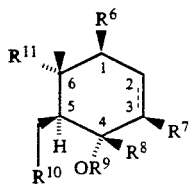

As previously defined, R$^6$ is hydroxyl or a protected hydroxyl; R$^7$ is hydrogen, hydroxyl, or a protected hydroxyl; R$^8$ is carboxyl, hydroxylmethyl, or a protected hydroxylmethyl; or R$^7$ and R$^8$ when taken together with carbon atoms 3 and 4, form an oxetane ring; or R$^6$ and R$^8$ when taken together with carbon atoms 1 and 4, form a bridged lactone; R$^9$ is hydrogen or a hydroxyl protecting group; R$^{10}$ is hydroxyl or a protected hydroxyl; or R$^8$ and R$^{10}$ when taken together with carbon atoms 4 and 5, form a γ-butyrolactone ring; R$^{11}$ is alkoxycarbonyl, formyl, a protected formyl, hydroxylmethyl or a protected hydroxylmethyl; or R$^6$ and R$^{11}$ when taken together with carbon atoms 1 and 6, form a 2,2-dimethyl-1,3-dioxane ring; and the dotted line between the 2- and 3-positions of the six-membered ring represents an optional bond. Thus, the compounds (6) encompass the CD ring units (9) and (11) and their functionally equivalent molecules.

Exemplary hydroxyl protecting group useful in compounds (6), in addition to those already enumerated, include p-toluensufonyl and methanesulfonyl, particularly for the R$^8$ value. As indicated earlier, where more than two hydroxyl protecting groups are present in the molecule, it is usually preferred that they be different in order to be chemically distinct. Preferred protected formyl groups are not different from those already enumerated. The "alkoxycarbonyl" group for the R$^{11}$ value preferably has from 2 to 11 carbons, including chiral groups such as I-mentholoxycarbonyl.

A preferred group of compounds of the compounds (6) are those wherein R$^7$ and R$^8$ form an oxetane. Especially favored within this group are the compounds wherein R$^9$ is a hydroxy protecting group and R$^{10}$ is a protected hydroxyl group. Still favored compounds are those wherein R$^{11}$ is formyl or 1,3-dithianyl.

A second preferred group of compounds are those wherein R$^7$ is hydroxyl or a protected hydroxyl. Especially favored within this group are the compounds wherein R$^{11}$ is hydroxylmethyl or a protected hydroxylmethyl. Still favored compounds are those wherein R$^8$ is methanesulfonyloxymethyl.

A third preferred group of compounds are those wherein there is a double bond between the 2- and 3-positions of the six-membered ring. Especially favored within this group are the compounds wherein R$^{11}$ is hydroxylmethyl or a protected hydroxymethyl. Another subgroup of preferred compounds are those wherein R$^{11}$ is alkoxycarbonyl and R$^6$ and R$^8$ form a bridged lactone ring or R$^8$ and R$^{10}$ form a γ-butyrolactone ring.

Some of the preferred individual compounds within the generic formula (6) are depicted hereinbelow:

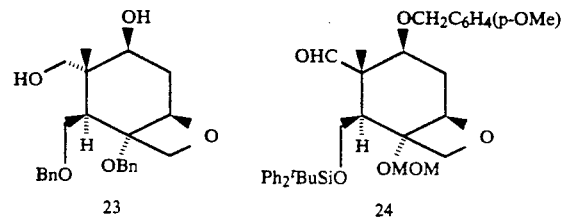

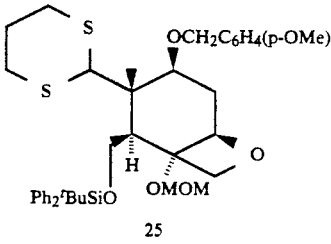

wherein Bn represents benzyl and MOM is as previously defined.

Since the compounds of formula (6) may have several asymmetric carbons, it is recognized by those skilled in the art that such compounds may exist in diastereomeric, racemic, or optically active forms. All of these forms are contemplated within the scope of this invention. More specifically, this invention includes enantiomers, diasteromers, racemic mixtures, and other mixtures thereof.

An exemplary synthesis of preferred compounds of formula (6) is illustrated hereinbelow. As before, the present scheme can also be used with modifications that are obvious to one skilled in the art to prepare the compounds of formula (6) with structures different from those which are depicted in the scheme.

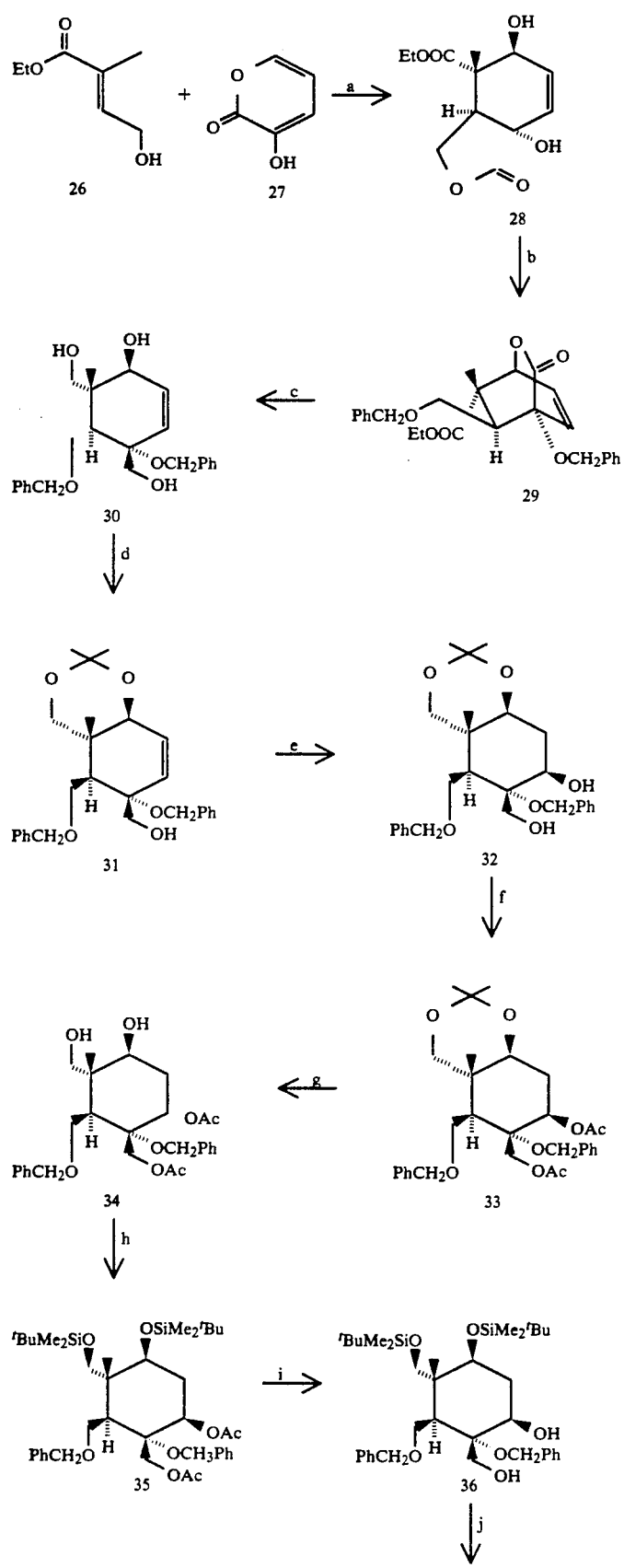

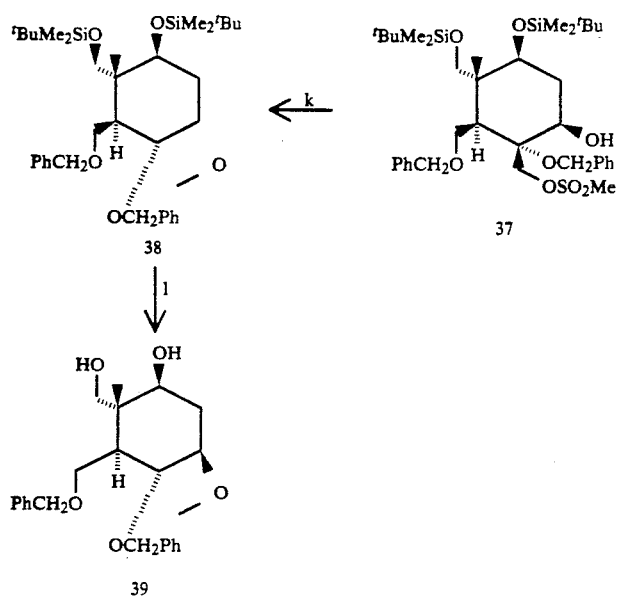

Scheme 2. Synthesis of Taxol Ring CD Unit

Reagents and conditions: (a) 1.0 equiv. of PhB(OH)$_2$, PhH, 90° C., 48 h; 1.0 equiv. of 2,2-dimethyl-1,3-propanediol, 25° C., 30 min, 61%; (b) 2.5 equiv. of KH, 2.5 equiv. of PhCH$_2$Br, THF, $^n$Bu$_4$NI (cat.), 0° C., 30 min then 25° C., 3 h, 80%; (c) 5.0 equiv. of RedAl, PhH-THF (9:1), reflux, 2 h, 92%; (d) excess of 2,2-dimethoxypropane, 0.1 equiv. of CSA, CH$_2$Cl$_2$ 25° C., 30 min., 100%; (e) 10.0 equiv. of BH$_3$.THF, CH$_2$Cl$_2$, 25° C., 1 h; excess of H$_2$O$_2$, excess of NaOH, 25° C., 30 min, 60%; (f) excess of Ac$_2$O, 2.5 equiv. of DMAP, CH$_2$Cl$_2$, 25° C., 30 min, 90%; (g) 0.1 equiv. of CSA, MeOH 25° C., 30 min., 100%; (h) 2.4 equiv. of BuMe$_2$SiOTf, 2.6 equiv. of 2,6-lutidine, CH$_2$Cl$_2$, 25° C., 30 min, 96%; (i) 3.0 equiv. of NaOMe, MeOH, 25° C., 3 h, 97%; (j) 1.2 equiv. of MeSO$_2$Cl, 2.0 equiv. of DMAP, CH$_2$Cl$_2$, 0° C., 2 h, 80%; (k) 5.0 equiv. of NaH, Et$_2$O, 45° C., 12 h, 95%; (l) 3.0 equiv. of $^n$Bu$_4$NF, THF, 25° C., 3 h, 90%.

The starting materials (26) and (27) can be prepared by conventional procedures.

Among many steps involved in the above sequence, the first step (a) is considered critical to this invention. The reaction, a Diels-Alder reaction between a diene (27) and a dienophile (26), is conducted in a reaction-inert solvent, preferably in the presence of a Lewis acid. Representative solvents are aromatic hydrocarbons such as benzene, xylene and toluene. The reaction is generally carried out at the reflux temperature of the solvent used. Suitable Lewis acids include dihydroxylphenylboron and diethylaluminum chloride. Under these conditions, reaction is complete within several days. For one mole of the diene (27), it is preferred to use an excess amount (e.g., 50% excess) of the dienophile (26). The reaction is highly regioselective, resulting in the formaton of a single regioisomeric intermediate (not depicted in the scheme) which undergoes translactonization to give a lactone (28). The structure of the lactone (28) has been confirmed by further derivation and x-ray crystallographic analysis. This Diels-Alder reaction creates correct (relative) stereochemistry at four carbon centers, positions 3, 4, 7 and 8 (numbering corresponds to the taxol ring).

Starting with an optically active derivative of the dienophile (26) (see, for instance, W. Oppolzer et al., Angew. Chem. Int. Ed. Eng., 1984, 23, 876), an optically active derivative of compound (28) can be prepared in a similar manner. Therefore, the whole reaction sequence can be carried out in optically active compounds. Alternatively, the racemic compound (29) may be resolved into the pure enantiomers prior to its conversion to a triol of formula (30). Such optical resolution techniques are known to those skilled in the art, and include: the formation and preferential crystallization of the desired diastereomer through the use of optically active alkaloids such as brucine; the formation of diastereomers and separation of the desired diastereomer through high performance column chromatography; and separation of the desired enantiomer by the use of optical active chromatography (e.g., I-methol impregnated).

All the products of formulae (28) through (39) in the sequence can be isolated and purified by conventional means.

The diol of formula (39) can be readily converted to an aldehyde of formula (24) or an equivalent molecule thereof (Ring CD unit). Once the aldehyde (24) is obtained, protection of the formyl group as 1,3-dithiane yields the compound of the formula (25), which is the desired Ring CD unit.

The importance of the compounds of formula (5) and formula (6) as key intermediates can be easily recognized in the synthesis of taxol, wherein the ring A units (13) and (14) and the ring CD units (24) and (25) are used. The scheme is depicted hereinbelow.

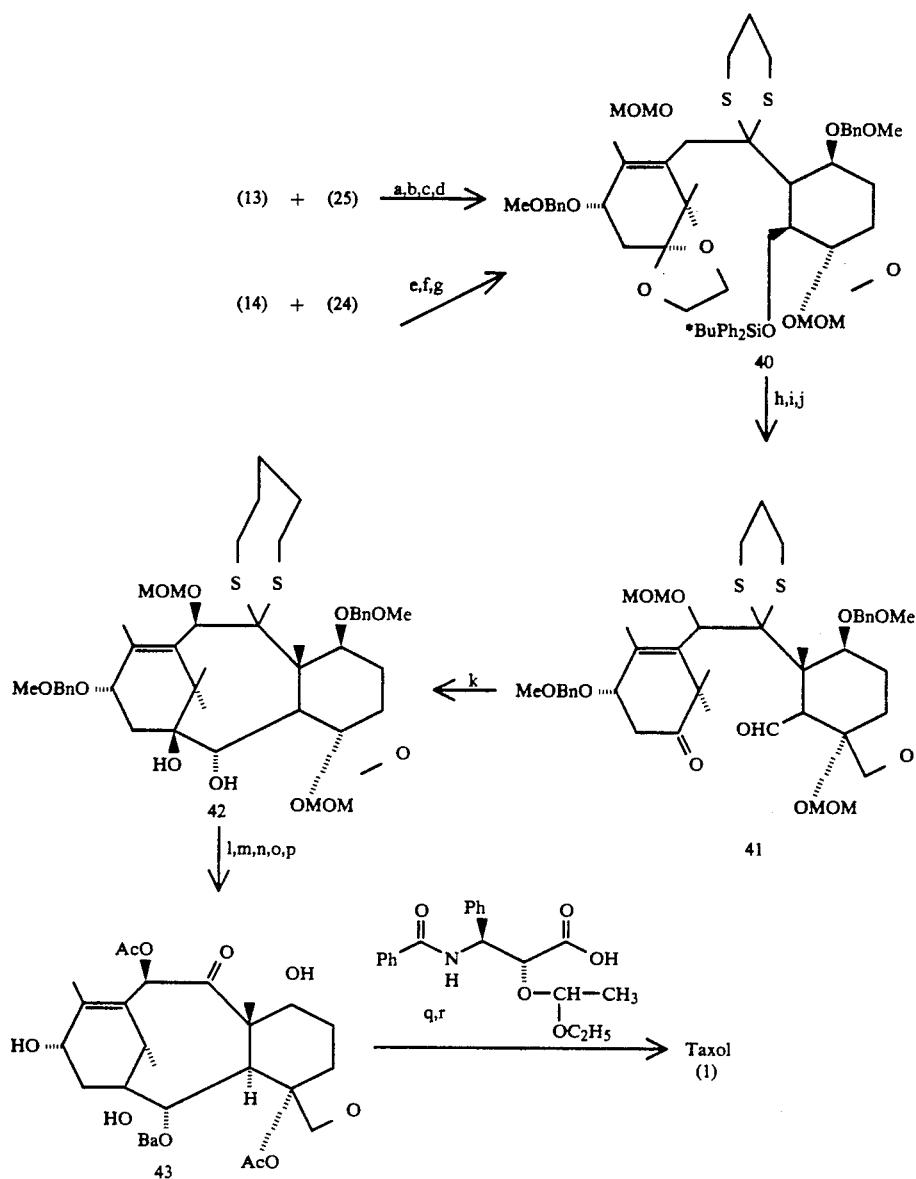

Scheme 3. Synthesis of Taxol

Conditions: (a) coupling reaction; (b) PCC; (c) Corey's asymmetric reduction; (d) MOMCl; (e) coupling reaction; (f) PCC; (g) 1,3-propanedithiol, $Zn(OTf)_2$; (h) TBAF; (i) CSA, MeOH; (j) PCC; (k) Ti(O), DME; (l) BzCl, DMAP; (m) HgCl, NCS; (n) 6NHCl; (o) $Ac_2O$, DMAP; (p) DDQ; (q) DCC, DMAP; (r) $H^+$.

In one method, coupling of the aldehyde (13) and a metallated derivative (with lithium) of formula (25), followed by oxidation, asymmetric reduction and alcohol protection, leads to a compound of formula (40).

In an alternate method the compound (40) can also be prepared by the coupling of the aldehyde (24) and the lithium compound (14), followed by oxidation and keto protection.

Further reaction involves the deprotection of the tert-butyldiphenylsilyl moiety as well as the deprotection of the 1,3-dioxolane moiety. Then, oxidation to form a ketoaldehyde of formula (41) ensues. Ti(O)-mediated coupling reaction (K) represents a key process for the formation of a taxol ring system to provide a compound of formula (42), and is a modification of the method described in J. E. McMurry et al., J. Org. Chem., 1989, 54, 3748.

A variety of protecting groups for the hydroxyl groups and the keto group present in the molecule (42) can easily be removed under standard conditions [steps (m) and (n)]. Benzoylation of the hydroxyl group at the 2-position [step (l)] and the acetylation of the hydroxyl groups at the 4- and 10-positions provides an immediate precursor (43) to taxol (1).

The final steps (q, r), the attachment of the $C_{13}$ ester side chain through the esterification of the C-13 alcohol with a (2R, 3S) 3-phenylisoserine derivative, have been reported by J. N. Denis et al., in J. Am. Chem. Soc., 1988, 100, 5917 and U.S. Pat. No. 4,924,011. An alternate approach to the attachment of the $C_{13}$ ester side chain has been described by R. A. Holton in U.S. Pat. No. 5,015,744.

Thus, the above reaction sequence completes the total synthesis of taxol, and correlates the taxol with the present intermediate (13)(14)(24) and (25) and other equivalent compounds embraced by this invention.

The above disclosure generally describes the present invention. A more complete understanding can be obtained by reference to the following specific examples which are provided to amplify the invention and are not to be construed as limiting its scope which is instead defined by the appended claims.

Proton nuclear magnetic resonance spectra (NMR) were measured at 500 MHz unless otherwise indicated for solutions in deuterochloroform ($CDCl_3$) and peak positions are expressed in parts per million (ppm) downfield from tetramethylsilane. The peak shapes are denoted as follows: s, singlet; d, doublet; t, triplet; q, quartet; m, multiplet; and b, broad.

EXAMPLE 1
PREPARATION OF COMPOUND (17)

A mixture of diene (15) (10 g, 59.5 mM) (obtained by reduction-acetylation of the corresponding ethyl ester; l. Alkonyi et al., supra) and 2-chloroacrylonitrile (16) (Cresent Chemical Co.) (7.8 g, 89.0 mM) was heated in a sealed tube at 135° C. for 48 hours. The crude product was purified by flash column chromatography (silica gel, 10% ether in petroleum ether) to give the compound (17) (12.2 g, 80%) as a colorless crystalline solid, mp 86°-88° C. (recrystallized from ether).

IR (neat): 2979, 2205, 1730, 1436, 1372, 1241 $cm^{-1}$.
$^1$HNMR: 4.62 (s, 2H), 2.44–2.29 (m, 4H), 2.06 (s, 3H), 1.72 (s, 3H), 1.39 (s, 3H), 1.25 (s, 3H).

EXAMPLE 2
PREPARATION OF COMPOUND (18)

A mixture of compound (17) (2.55 g, 10 mM) and KOH (2.8 g, 50 mM) in tBuOH (30 ml) was heated to 65° C. for 3 hours. The reaction mixture was allowed to cool to room temperature, quenched with $NH_4Cl$ (20 ml), extracted with ethylacetate (300 ml) and the solvent evaporated to give 2-dimethyl-3-hydroxymethyl-4-methyl-cyclohex-3-enelone. (1.51 g). The product without further purification was dissolved in $CH_2Cl_2$ (10 ml) at 0° C. DMAP (1.1 g, 9 mM) and $AC_2O$ (0.67 ml, 7.5 mM) were added to the mixture. The reaction mixture was stirred at 0° C. for 25 minutes, quenched with methanol (2 ml) and $NH_4Cl$ (10 ml). The organic material was extracted with ether (100 ml). Removal of the solvent and purification by flash column chromatography (silica gel, 20% ether in petroleum ether) gave compound (18) (1.28 g, 61%).

IR (neat): 2973, 2926, 1735, 1710, 1233 $cm^{-1}$.
$^1$HNMR: 4.6 (s, 2H), 2.6 (t, J=7.2 $H_z$, 2H), 2.4 (t, J=7.1 $H_z$), 2.1 (s, 3H), 1.8 (s, 3H), 1.1 (s, 6H).

EXAMPLE 3
PREPARATION OF COMPOUND (19)

A mixture of compound (18) (2.1 g, 10 mM), ethylene glycol (5 ml), CSA (100 mg) and 4 Å molecular sieves in benzene (50 ml) was heated at 70° C. for 3 hours. The reaction mixture was allowed to cool to room temperature. Removal of the solvent, followed by flash column chromatography (silic gel, 5% ethylacetate in benzene) provided compound (19) (2.29 g, 90%).

IR (neat): 2924, 1724, 1237 $cm^{-1}$.

$^1$HNMR: 4.6 (s, 2H), 4.0 (m, 4H), 2.2 (t, J=7.2 $H_z$, 2H), 2.1 (s, 3H), 1.8 (t, J=7.2 $H_z$, 2H), 1.7 (s, 3H), 1.1 (s, 6H).

EXAMPLE 4
PREPARATION OF COMPOUND (20)

A mixture of compound (19) (1.27 g, 5 mM) and $SeO_2$ (1.11 g, 10 mM) in 1,4-dioxane (50 ml) was heated at 100° C. for 2 hours. The reaction mixture was allowed to cool, and the solvent was removed under reduced pressure. The residue was filtered through filter paper to obtain 3-acetyloxymethyl 4-dimethyl-2-methyl-5-1,3-dioxolanyl-2-cyclohexene-1-ol. To the crude product in $CH_2Cl_2$ (30 ml) was added predried 4 Å molecular sieves (1 g) and PCC (2.16 g, 10 mM) sequentially. The reaction mixture was then stirred at room temperature for 1 hour before filtering through a pad of celite. Removal of the solvent, followed by flash column chromatography (silica gel, 40% ether in petroleum ether) provided compound (20) as a colorless oil (1.01 g, 75% overall yield).

IR (neat): 2978, 2884, 1737, 1672, 1652, 1226 $cm^{-1}$.
$^1$HNMR: 4.81 (s, 2H), 3.95 (m, 4H), 2.75 (s, 2H), 2.10 (s, 3H), 1.84 (s, 3H), 1.20 (s, 6H).

EXAMPLE 5
PREPARATION OF COMPOUND (21)

Catecholborane (6.00 ml, 1M in THF solution, 6.0 mM) was added dropwise to a stirred toluene (15 ml) solution of the ketone (20) (960 mg, 30 mM) and Corey's (R)-oxazaboroline (76 mg, 0.3 mM) at −78° C. The reaction mixture was stirred at −78° C. for 10 minutes and then quenched with water (1 ml). The quenched mixture was allowed to warm to ambient temperature, and extracted with ether (2×50 ml). Removal of the solvent gave essentially pure compound (22) (918 mg, 95% yield, ≧98% ee by Mosher ester NRM analysis as a colorless oil; J. A. Dale, et al., *J. Org. Chem.*, 1969, 9, 2543).

IR (neat): 3439, 2921, 1732, 1223 $cm^{-1}$.
$^1$HNMR: 4.61, 4.58 (2×d, J=12.8 Hz, 2×1H), 4.10–3.82 (m, 4H), 3.94 (bm, 1H), 3.12 (bd, J=11 Hz, 1H), 2.15 (dd, J=5.5, 13.2 Hz, 1H), 2.05 (s, 3H), 1.95 (dd, J=3.1, 13.2 Hz, 1H), 1.82 (s, 3H), 1.08 (s, 3H), 1.02 (s, 3H).

EXAMPLE 6
PREPARATION OF COMPOUND (22)

To a mixture of compound (21) (1.18 g, 5 mM) and 2,6-lutidine (0.94 ml, 8 mM) in $CH_2Cl_2$ (10 ml) at 0° C. was added dropwise tert-butyldimethyltriflate (1.44 ml, 6 mM). The reaction mixture was then allowed to stir at 0° C. for 1 hour, diluted with ether (100 ml), and quenched with $NH_4Cl$ (10 ml). Extraction with dichloromethane and evaporation of the solvent provided compound (12).

$^1$HNMR: 4.6 (m, 2H), 4.31–4.27 (m, 1H), 4.02–3.90 (m, 4H), 2.1 (s, 3H), 2.0–1.9 (m, 2H), 1.72 (s, 3H), 1.13, 0.96 (2×s, 2×3H), 0.9 (s, 9H), 0.1 (2×s, 2×3H).

EXAMPLE 7
PREPARATION OF COMPOUND (12)

To a solution of compound (22) (1.25 g, 5 mM) in acetone (10 ml) and $H_2O$ (1 ml) was added p-toluenesulfonic acid monohydrate (286 mg, 1.5 mM). The reaction mixture was then allowed to stir at ambient temperature for 12 hours. Removal of the solvent, followed by flash column chromatography provided compound (21) (767 mg, 65%).

¹HNMR: 4.65-4.57 (q, 2H), 4.31-4.27 (m, 1H), 2.76-2.70 (dd, J=4.1, 11.6 H$_z$), 2.64-2.59 (dd, 5.5, 11.6 H$_z$), 2.02 (s, 3H), 1.80 (s, 3H), 1.19, 110 (2×s, 2×3H), 0.83 (s, 9H), 0.1 (s, 6H).

EXAMPLE 8

PREPARATION OF COMPOUND (28)

To a solution of hydroxypyrone (27) (R. H. Wiley et al., *J. Am. Chem. Soc.*, 1956, 78, 2398) (1.52 g, 13.6 mM) and phenyl-boronic acid (1.7 g, 13.9 mM) in benzene (30 ml) was added to the dienophile (26) (prepared in ca. 70% overall yield from allyl alcohol by the following sequence: (i) silylation with $^t$BuPh$_2$SiCl-imidazole; (ii) ozonolysis; (iii) condensation with Ph$_3$P=CH(CH$_3$)CO$_2$C$_2$H$_5$; and (iv) desilylation using $^n$Bn$_4$NF) (1.44 g, 10.0 mM). The solution was refluxed for 48 hours with azeotropic removal of water. After the solution was cooled to room temperature, 2,2-dimethyl-1,3-propanediol (1.45 g, 13.8 mM) was added and the solution was stirred for 30 minutes. The solvent was removed under reduced pressure and the crude product was purified by flash column chromatography (silica gel, 10% petroleum ether in ethylacetate) to afford compound (28) (1.56 g, 60.9%) as a light yellow oil.

IR (neat): 3441, 2979, 1777, 1727 cm$^{-1}$.

¹HNMR (300 MHz): 6.09 (dd, J=4.0, 10.0 Hz, 1H), 5.82 (br d, J=10.0 Hz, 1H), 4.63-4.58 (m, 2H, CH—OH), 4.45 (dd, J=8.2, 9.3 Hz, 1H), 4.18 (q, J=7.1 Hz, 2H), 3.70 (br, 1H), 3.10 (dd, J=7.7 Hz, 1H), 2.55 (br, 1H), 1.29 (s, 3H), 1.26 (t, J=7.1 Hz, 3H).

EXAMPLE 9

PREPARATION OF COMPOUND (29)

To a suspension of KH (35%, 3.4 g, 29.75 mM) in THF (10 ml) was added the lactone (28) (3.09 g, 12.07 mM) in THF (15 ml) at 0° C. under argon atmosphere. After stirring for 30 minutes, BnBr (98%, 5.1 g, 29.93 mM) and tBu$_4$N (cat.) were added, and the mixture was stirred for 3 hours at room temperature. The reaction mixture was then cooled to 0° C., and the excess KH was quenched by careful addition of sat. NH$_4$Cl and extracted with ether (50 ml×3). The organic layer was dried over Na$_2$SO$_4$ and the solvent removed under reduced pressure. The resulting oil was purified by flash column chromatography (silica gel, 10% ether in petroleum ether) to yield compound (29) (4.25 g, 80.8%) as a light yellow oil.

IR (neat): 2935, 1776, 1727 cm$^{-1}$.

¹HNMR (300 MHz): 7.27 (M, 10H, ArH), 6.24 (dd, J=2.9, 10.2 Hz, 1H), 6.00 (dd, J=1.9, 10.2 Hz, 1H), 4.66 and 4.49 (AB quartet, J=10.6 Hz, 2H), 4.62 and 4.48 (AB quartet, J=11.7 Hz, 2H), 4.45 (dd, J=1.9, 2.9 Hz, 1H), 4.33 (m, 2H), 4.05 and 3.90 (m, 2H), 3.19 (dd, J=5.1, 7.30, 1H), 1.21 (s, 3H), 1.08 (t, J=7.2H$_z$, 3H).

EXAMPLE 10

PREPARATION OF COMPOUND (30)

To a solution of compound (29) (3.50 g, 8.03 mM) in a mixture of 45 ml of benzene and 5 ml of THF was added Red-Al (11.8 ml, 3.4M solution in toluene, 40.12 mM) at room temperature. The mixture was then heated to a gentle reflux for 2 hours. After cooling to 0° C., the excess Red-Al was quenched by careful addition of sat. sodium potassium tartrate, and the mixture was then extracted with three portions of ether. The combined organic extracts were dried over Na$_2$SO$_4$, then filtered and concentrated to provide the crude product. Flash column chromatography (silica gel, 50% ether in petroleum ether, ~100% ether) gave compound (30) as a white foam (2.93 g, 91.7%).

IR (neat): 3382, 2881, 1046 cm$^{-1}$.

¹HNMR (300 NHz); 7.32 (M, 10H), 6.17 (dd, J-2.4, 10.5 Hz, 1H), 5.85 (dd, J=4.0, 10.5 Hz, 1H), 4.75 and 4.60 (AB quartet, J=11.7 Hz, 2H), 4.45 and 4.40 (AB quartet, J=11.0 Hz, 2H), 3.99 (m, O$_2$H), 3.87 (m, 1H), 3.73 (s, br), 3.61 and 3.42 (AB quartet, J=11.3 Hz, 2H), 2.90~2.30 (br, 3H), 2.23 (m, 1H), 0.97 (s, 3H).

EXAMPLE 11

PREPARATION OF COMPOUND (31)

To a solution of compound (30) (3.20 g, 8.00 mM) in 80 ml of dry CH$_2$Cl$_2$ was added 2,2-dimethoxypropane (98%, 1.0 g, 9.4 mM) and CSA (0.19 g, 0.8 mM). The resulting solution was stirred for 30 minutes at room temperature under argon, and then quenched with sat. NaHCO$_3$. The aqueous layer was extracted with two additional portions of CH$_2$Cl$_2$ and the combined organic extracts were dried over Na$_2$SO$_4$. Filtration and concentration provided compound (31) as a white foam (3.50 g, 100%).

IR (neat): 3566, 2978, 1061 cm$^{-1}$.

¹HNMR (300 MHz): 7.31 (m, 10H), 6.09 (dd, J=1.1, 10.5 Hz, 1H), 5.83 (dd, J=2.3, 10.5 Hz, 1H), 4.72 and 4.47 (AB quartet, J=11.8 Hz, 2H), 4.45 and 4.35 (AB quartet, J=11.1 Hz, 2H), 3.90 (dd, J=2.9, 12.3 Hz, 1H), 3.79 (dd, J=10.3, 12.2 Hz), 3.72~3.40 (m, 5H), 2.08 (dd, J=2.9, 10.2 Hz, 1H), 1.58 (br, 1H), 1.35 and 1.23 (s, 6H, 3H×2), 0.97 (s, CH$_3$).

EXAMPLE 12

PREPARATION OF COMPOUND (32)

To a magnetically stirred solution of compound (31) 56 mg, 0.13 mM) in 1.5 ml of dry CH$_2$Cl$_2$ at 0° C. was added BH$_3$-THF (1.3 ml, 1.0M solution in THF, 1.3 mM). The solution was allowed to warm slowly to room temperature and stirred for 1 hour. The clear, colorless solution was then cooled to 0° C., and the excess diborane was quenched by the addition of H$_2$O$_2$ (1 ml, 30%) and 3N NaOH (1 ml). After stirring for 30 minutes at room temperature, 20 ml of CH$_2$Cl$_2$ was added, and the solution was washed with H$_2$O, and sat. NH$_4$Cl. The aqueous layer was separated and washed with two portions of CH$_2$Cl$_2$ and the organic layer were combined and dried over Na$_2$SO$_4$. The solvent was removed under reduced pressure and crude product was purified by preparative TLC to give compound (32) as a white foam (34.8 mg, 59.6%).

IR (neat): 3398, 2924, 1453, 1369, 1219, 1063 cm$^{-1}$.

¹HNMR (300 MHz): 7.41-7.28 (m, 10H), 4.66 and 4.39 (AB quartet, J=11.8 Hz, 2H), 4.64 and 4.56 (AB quartet, J=10.1 Hz, 2H), 4.10 and 3.52 (AB quartet, br, J=12.0 Hz, 2H), 4.05 (dd, J=4.4, 12.6 Hz, 1H), 3.86 (dd, J=2.2, 12.3 Hz, 1H), 3.80 (dd, J=7.0, 12.3 Hz, 1H), 3.71 and 3.40 (AB quartet, J=11.6 Hz, 2H), 3.07 (dd, J=4.1, 11.5 Hz, 1H), 2.47 (ddd, J=4.1, 4.4, 12.2 Hz, 1H), 1.85 (ddd, J=12.2 Hz, 1H), 1.72 (dd, J=2.2, 7.0 Hz, 1H), 1.34 (s, 3H), 1.15 (s, 3H).

EXAMPLE 13

PREPARATION OF COMPOUND (33)

To a solution of Compound (32) (260 mg, 0.57 mM) in 5 ml of dry $CH_2Cl_2$ was added $Ac_2O$ (175 mg, 1.72 mM) and DMAP (243 mg, 1.99 mM). After stirring this mixture for 30 minutes at room temperature under argon, the solvent was removed under reduced pressure and the crude product was purified by column chromatography (silica gel, 30% ether in petroleum ether) to afford compound (33) (277.1 mg, 90.0%).

$^1$HNMR (300 MHz); 7.30 (m, 10H), 5.19 (dd, J=5.0, 12.3 Hz, 1H), 4.65–4.33 (m, 6H), 3.94 (m, 2H), 3.70 and 3.42 (AB quartet. J=11.7 Hz, 2H), 3.16 (dd, J=4.5, 11.6 Hz, 1H), 2.36 (m, 1H), 2.10 and 2.03 (s, 6H), 1.78–1.60 (m, 2H), 1.33 and 1.29 (s, 6H, $CH_3 \times 2$), 1.14 (s, 3H).

EXAMPLE 14

PREPARATION OF COMPOUND (34)

A mixture of compound (33) (277 mg, 0.51 mM) and CSA (135 mg, 0.058 mM) in MeOH (10 ml) was stirred for 30 minutes at room temperature under argon. The reaction was then diluted with 100 ml of ether, washed with $H_2O$, brine and dried over $Na_2SO_4$. After solvent removal, the product was purified by flash column chromatography (silica gel, 60%–75% ether in petroleum ether) to give compound (34) as white foam (255 mg, 99.4%).

$^1$HNMR (300 MHz), 7.31 (m, 10H), 5.28 (dd, J=5.0, 12.2 Hz, 1H), 4.65 and 4.49 (AB quartet. J=11.6 Hz, 2H), 4.58 and 4.52 (AB quartet. J=10.8 Hz, 2H), 4.48 and 4.37 (AB quartet. J=12.8 Hz, 2H), 4.24 (d, J=10.9 Hz, 1H), 3.84 (dd, J=7.2, 10.9 Hz, 1H), 3.70 (dd, J=4.5, 11.8 Hz, 1H), 3.64 and 3.45 (AB quartet. J=11.8 Hz, 2H), 3.38 (ddd, J=4.7, 12.7 Hz, 1H), 2.19 (d, J=7.2 Hz, 1H), 2.05 (s, 6H), 1.74 (ddd, J=12.3 Hz, 1H), 0.87 (s, 3H).

EXAMPLE 15

PREPARATION OF COMPOUND (35)

To a solution of compound (34) (56.0 mg, 0.11 mM) in dry $CH_2Cl_2$ (10 ml) was added $tBuMe_2SiOTf$ (69.7 mg, 0.25 mM) and 2,6-lutidine (30.6 mg, 0.29 mM). The reaction mixture wa stirred for 30 minutes at room temperature under argon. After solvent removal, the crude product was purified by column chromatography to give compound (35) (7.8 mg, 95.6%).

$^1$HNMR (300 MHz): 7.28 (m, 10H), 5.17 (dd, J=4.8, 10.2 Hz, 1H), 4.70 and 4.61 (AB quartet. J=12.6 Hz, 2H), 4.59 and 4.40 (AB quartet. J=11.5 Hz, 2H), 4.54 and 4.42 (AB quartet. J=11.2 Hz, 2H), 3.96 (d, J=3.8 Hz, 2H), 3.75 (dd, J=4.0, 11.0 Hz, 1H), 3.63 and 3.55 (AB quartet. J=9.5 Hz, 2H), 2.26 (m, 2H), 2.03 and 1.98 (s, 6H), 1.93 (m, 1H), 1.05 (s, 3H), 0.89 (s, 18H), 0.04 (s, 12H).

EXAMPLE 16

PREPARATION OF COMPOUND (36)

To a solution of compound (35) (37.3 mg, 0.051 mM) in 1 ml of dry $CH_2Cl_2$ was added NaOMe (8.3 mg, 0.153 mM). The mixture was stirred for 3 hours at room temperature under argon. Dichloromethane (10 ml) was added, the solution washed with $H_2O$, brine and then dried over $Na_2SO_4$. The solvent was removed under reduced pressure to provide compound (36) as white foam (32.2 mg, 97.3%).

$^1$HNMR: 7.32 (m, 10H), 4.70 and 4.49 (AB quartet. J=11.0 Hz, 2H), 4.64 and 4.42 (AB quartet. J=11.5 Hz, 2H), 4.26 and 4.20 (AB quartet. J=12.0 Hz, 2H), 4.07 (dd, J=2.5, 11.5 Hz, 1H), 3.90 (dd, J=4.5, 12.0 Hz, 1H), 3.85 (dd, J=4.3, 12.0 Hz, 1H), 3.62 (br, 1H), 3.58 (dd, J=4.0, 11.0 Hz, 1H), 3.50 (br, 1H), 2.86 (m, 1H), 1.99 (m, 1H), 1.86 (ddd, J=11.0, 1H), 1.01 (s, 3H), 0.89 and 0.88 (s, 18H), 0.05 (s, 6H), 0.02 and 0.01 (s, 6H).

EXAMPLE 17

PREPARATION OF COMPOUND (37)

To a mixture of compound (36) (170 mg, 0.26 mM) and DMAP (65 mg, 0.52 mM) in $CH_2Cl_2$ (5 ml) at 0° C. was added MsCl (24 μl, 0.32 mM). The reaction mixture was then allowed to stir for 2 hours, diluted with ether (80 ml) and quenched with $NH_4Cl$ (10 ml). The organic compound was extracted with $CH_2Cl_2$, the solvent removed under reduced pressure. The crude product was purified by flash column chromatography to afford compound (37) (150 mg, 80%).

$^1$HNMR: 7.30 (m, 10H), 4.87 and 4.85 (AB q. J=11.2 Hz, 2H), 4.66 and 4.44 (AB q. J=11.0 Hz, 12H), 4.54 and 4.50 (AB q. J=10.0 Hz, 2H), 3.96 (m, 2H), 3.85 (dd, J=6.5, 11.3 Hz, 5H), 3.68 (br, 1H), 3.61 (dd, J=3.2, 8.0 Hz, 1H), 3.48 (br, 1H), 2.93 (s, 3H), 2.22 (d.br, 1H), 2.09 (br, 1H), 2.00 (m, 1H), 1.10 (s, 3H), 0.85 and 0.90 (s, 18H), 0.08 and 0.07 (s, 12H).

EXAMPLE 18

PREPARATION OF COMPOUND (38)

To the solution of compound (37) (143 mg, 0.2 mM) in ether (25 ml) at 25° C. was added NaH (40 mg, 1.0 mM, 60% weight in oil). The reaction mixture was then heated to 45° C. using sealed cap for 12 hours and was allowed to cool to room temperature. The solvent was removed under reduced pressure. The crude product was purified by flash column chromatography to afford compound (38) (118 mg, 95%).

$^1$HNMR: 7.35 (m, 10H), 4.92 and 4.52 (AB q. J=6.9 Hz, 2H), 4.88 (dd, J=4.3, 8.6 Hz, 1H), 4.66 and 4.40 (AB q. J=12.2 Hz, 2H), 4.59 and 4.55 (AB q. J=12.5 Hz, 2H), 3.85 (m, 2H), 3.56 and 3.46 (AB q. J=10 Hz, 2H), 4.52 (dd, J=4.0, 8.0 Hz, 1H), 2.27 (m, 1H), 2.12 (m, 2H), 1.15 (s, 3H), 0.88 and 0.89 (s, 18H), 0.08 and 0.06 (s, 12H).

EXAMPLE 19

PREPARATION OF COMPOUND (39)

$^nBu_4NF$ (0.3 ml, 0.3 mM, 1M solution in THF) was slowly added to the solution of compound (39) (62.6 mg, 0.1 mM) in THF (2 ml) at 25° C. The reaction mixture was allowed to stir for 3 hours. The solvent was removed under reduced pressure. The crude product was purified by flash column chromatography to afford compound (39) (35.8 mg, 90%).

IR (neat): 3450, 2980, 2870, 1465, 1072 cm$^{-1}$.

$^1$HNMR ($C_6D_6$): 7.57–7.32 (m, 10H), 5.09 (dd, J=3.2, 8.6 Hz, 1H), 4.75, 4.63 (2d, J=7.5 Hz, 2H), 4.70, 4.55 (2d, J=11.6, 2H), 4.70, 4.54 (2d, J=11.7 Hz, 2H), 3.94, 3.64 (2d, J=11.1 Hz, 2H), 3.80 (dd, J=6.3, 10.7 Hz, 1H), 3.70 (m, 2H), 2.47 (t, J=5.9 Hz, 1H), 2.40 (m, 1H), 2.32 (m, 1H), 1.36 (s, 3H).

The invention now being fully described, it will be apparent to one of ordinary skill in the art that many changes and modifications can be made without departing from the spirit or scope of the invention.

We claim:

1. A compound of the formula

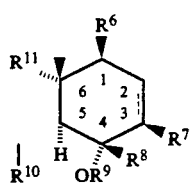

wherein $R^6$ is hydroxyl or a protected hydroxyl; $R^7$ and $R^8$, taken together with carbon atoms 3 and 4, form an oxetane ring; $R^9$ is hydrogen or a hydroxyl protecting group; $R^{10}$ is hydroxyl or a protected hydroxyl; $R^{11}$ is alkoxycarbonyl, formyl, a protected formyl, hydroxylmethyl or a protected hydroxylmethyl.

2. The compound according to claim 1, wherein $R^9$ is a hydroxyl protecting group and $R^{10}$ is a protected hydroxyl group.

3. The compound according to claim 1, wherein $R^{11}$ is a hydroxylmethyl or a protected hydroxylmethyl.

* * * * *